(12) United States Patent
Tuckman

(10) Patent No.: US 11,766,169 B2
(45) Date of Patent: Sep. 26, 2023

(54) APPARATUS FOR FACILITATING ACQUISITION OF A SCAN AND INTRAORAL SCANNING PROCEDURES

(71) Applicant: Implant Solutions Pty Ltd, Mulgrave (AU)

(72) Inventor: Michael Tuckman, Mulgrave (AU)

(73) Assignee: IMPLANT SOLUTIONS PTY LTD, Mulgrave (AU)

( * ) Notice: Subject to any disclaimer, the term of this patent is extended or adjusted under 35 U.S.C. 154(b) by 0 days.

(21) Appl. No.: 17/890,914

(22) Filed: Aug. 18, 2022

(65) Prior Publication Data

US 2023/0139288 A1 May 4, 2023

Related U.S. Application Data

(63) Continuation of application No. 17/753,928, filed as application No. PCT/AU2020/051004 on Sep. 30, 2020.

(30) Foreign Application Priority Data

Nov. 4, 2019 (AU) ................................ 2019904154

(51) Int. Cl.
*A61B 1/24* (2006.01)
*A61B 90/00* (2016.01)
(Continued)

(52) U.S. Cl.
CPC ................. *A61B 1/24* (2013.01); *A61B 90/39* (2016.02); *A61C 8/0089* (2013.01); *A61C 9/0053* (2013.01)

(58) Field of Classification Search
CPC ......... A61B 1/24; A61B 90/39; A61C 8/0089; A61C 9/0053
See application file for complete search history.

(56) References Cited

U.S. PATENT DOCUMENTS 4,767,328 A 8/1988 Branemark
4,784,608 A 11/1988 Mays
(Continued)

FOREIGN PATENT DOCUMENTS

AU 2012367264 A1 * 9/2014 ............... A61B 1/24
CN 113712695 A * 11/2021
(Continued)

OTHER PUBLICATIONS

EP European Search Report in European Appln. No. 19848244.0, dated Jul. 18, 2022, 8 pages.
(Continued)

*Primary Examiner* — Nicholas D Lucchesi
*Assistant Examiner* — Hao D Mai
(74) *Attorney, Agent, or Firm* — Fish & Richardson P.C.

(57) ABSTRACT

The present disclosure relates to scan gauges, a kit of scan gauges, and methods for facilitating the acquisition of a scan during an intraoral scanning procedure using an intraoral scanner, including: an elongate body having an attachment portion configured to attach the elongate body with an implant in a patient's mouth, the implant having a longitudinal axis, whereby the elongate body is adapted to extend substantially perpendicular to the longitudinal axis of the implant when mounted to the implant; the elongate body having a substantially planar upper surface and one or more side walls extending downwardly away from the upper surface; wherein the upper surface and the one or more side walls are observable in a resulting scan when the intraoral scanner scans the apparatus in a direction perpendicular to the upper surface.

14 Claims, 6 Drawing Sheets

(51) Int. Cl.
*A61C 8/00* (2006.01)
*A61C 9/00* (2006.01)

(56) References Cited

U.S. PATENT DOCUMENTS

| | | | |
|---|---|---|---|
| 5,431,567 A * | 7/1995 | Daftary | A61C 8/008 433/172 |
| 5,503,557 A | 4/1996 | Sillard | |
| 5,829,977 A * | 11/1998 | Rogers | A61C 8/0066 433/172 |
| 6,108,497 A * | 8/2000 | Nakayama | G01S 17/87 396/429 |
| D612,056 S * | 3/2010 | White, III | D24/156 |
| 8,612,037 B2 * | 12/2013 | Powell | B33Y 80/00 433/172 |
| 9,357,927 B2 * | 6/2016 | Thomsen | A61C 8/0001 |
| 9,566,138 B2 | 2/2017 | Fisker | |
| 10,524,880 B2 | 1/2020 | Wen | |
| 10,695,144 B2 * | 6/2020 | Dos Santos Redinha | A61B 90/39 |
| D946,757 S | 3/2022 | Mirelez, Jr. et al. | |
| D946,758 S | 3/2022 | Mirelez, Jr. et al. | |
| D961,083 S | 8/2022 | Abenaim | |
| D967,431 S | 10/2022 | Kim et al. | |
| D967,432 S | 10/2022 | Kim et al. | |
| D970,010 S | 11/2022 | Abenaim | |
| 2002/0039717 A1 * | 4/2002 | Amber | A61B 1/24 433/172 |
| 2003/0219148 A1 * | 11/2003 | Scharlack | A61C 9/0046 382/128 |
| 2006/0072810 A1 * | 4/2006 | Scharlack | G06F 18/00 382/154 |
| 2006/0223029 A1 | 10/2006 | Berger | |
| 2007/0281278 A1 * | 12/2007 | Jorneus | A61C 8/0069 433/173 |
| 2008/0057476 A1 * | 3/2008 | Zettler | A61C 8/0066 433/173 |
| 2008/0176188 A1 * | 7/2008 | Holzner | A61C 9/0053 433/215 |
| 2010/0179420 A1 | 7/2010 | Ernst | |
| 2010/0268071 A1 | 10/2010 | Kim | |
| 2012/0295223 A1 * | 11/2012 | Robb | A61C 8/006 433/173 |
| 2013/0196290 A1 * | 8/2013 | Herrington | A61C 8/0068 433/173 |
| 2014/0205969 A1 * | 7/2014 | Marlin | A61C 8/0068 433/196 |
| 2015/0196372 A1 | 7/2015 | Champleboux et al. | |
| 2016/0213442 A1 | 7/2016 | Geier | |
| 2017/0151038 A1 | 6/2017 | Fan et al. | |
| 2017/0348077 A1 | 12/2017 | Bullis et al. | |
| 2017/0354483 A9 | 12/2017 | Lawitschka et al. | |
| 2018/0000568 A1 | 1/2018 | Berger | |
| 2018/0008384 A1 | 1/2018 | Schulter et al. | |
| 2018/0235734 A1 | 8/2018 | Fan et al. | |
| 2018/0250102 A1 | 9/2018 | Schulter et al. | |
| 2018/0325631 A1 | 11/2018 | Christiansen et al. | |
| 2019/0117351 A1 | 4/2019 | Geier | |
| 2019/0290407 A1 | 9/2019 | Suttin et al. | |
| 2021/0386529 A1 | 12/2021 | Tuckman | |
| 2022/0160478 A1 | 5/2022 | Mirelez, Jr. et al. | |

FOREIGN PATENT DOCUMENTS

| | | | |
|---|---|---|---|
| EP | 3868332 A1 * | 8/2021 | A61C 13/0022 |
| KR | 20190040590 A * | 4/2019 | |
| KR | 20210131632 A * | 11/2021 | |
| WO | WO 1997/049351 | 12/1997 | |
| WO | WO-2009078424 A1 * | 6/2009 | A61B 90/39 |
| WO | WO-2017072653 A1 * | 5/2017 | |
| WO | WO-2017085288 A1 * | 5/2017 | A61C 8/0001 |
| WO | WO 2017/156405 | 9/2017 | |

OTHER PUBLICATIONS

PCT International Preliminary Report on Patentability in International Appln. No. PCT/AU2019/051222, dated May 20, 2021, 7 pages.

PCT International Preliminary Report on Patentability' in International Appln. No. PCT/AU2020/051044, dated May 19, 2022, 6 pages.

PCT International Search Report and Written Opinion in International Appln. No. PCT/AU2019/051222, dated Jan. 17, 2020, 12 pages PCT International Search Report and Written Opinion in International Appln. No. PCT/AU2020/051044, dated Oct. 27, 2020, 12 pages.

* cited by examiner

APPARATUS FOR FACILITATING ACQUISITION OF A SCAN AND INTRAORAL SCANNING PROCEDURES

FIELD

The present invention generally relates to an apparatus for facilitating acquisition of a scan in a patient's mouth and a related intraoral scanning procedure.

BACKGROUND

An implant impression is the main reference of an implant's location within a patient's mouth and is the foundation for designing and manufacturing any prosthetic framework. The accuracy of the implant impression depends on a number of factors. These factors include the number, the depth, and angulation of the implants, the impression technique selected, and the type of impression material. Deciding on the impression technique involves consideration of various options, including selecting a direct or indirect method, selecting a splinted or non-splinted solution, selecting the design of impression coping used, and selecting the type of impression tray (eg. open/closed).

Any inaccuracy during the impression-taking stage will be transferred to the model created. For this reason, an accurate implant impression is pivotal to the generation of an accurate definitive prosthetic model, which is the principal source for the fabrication of an accurately fitting milled prosthesis. The accurate fit at a clinical-stage of a milled prosthesis with the implant(s) fixed in the patient's jaw (and projecting into the patient's mouth) depends directly on the accuracy of the impression technique. An inaccurate fit between the implants and the prosthetic framework may give rise to a number of problems, including causing internal stresses within the framework, implants, prosthetic screws and bone. The selection options available with regard to conventional implant impressions can also result in variation in the results, depending on the experience of the operators and choice of materials used. Further, the orientation of the implant(s) in the arch can impact on the accuracy of conventional implant impressions. For example, relatively angled implants can give rise to loss of accuracy for conventional impressions, compared with parallel placement of implants.

The introduction and improvement of intraoral scanning technology has opened the door for the common acquisition of digital dental impressions. A digital impression becomes an alternative that reduces the possible sources of error associated with conventional implant impression methods. Digital impression systems are becoming more common because they allow the capture of digital data that can then be used to replicate the intraoral hard and soft tissues, replacing the need for impression trays and impression materials.

However, the accuracy of recording multiple implant positions across the arch placed on edentulous patients is a common challenge that affects the consistency of the results. The different intraoral scanner solutions in the market present different data acquisition systems and employ different knitting algorithms in compiling the complete data sets, which can cause variations in the scan information. Some of the factors that affect the accuracy of digital implant impressions are the different scanning protocols, optical settings of the scanning devices and the limitations of different technologies (blue/white light, video scanners, etc.).

It would be desirable to provide a solution to one or more of the drawbacks generally associated with acquisition of digital dental impressions. Alternatively, it would be desirable to provide an alternative means of acquiring more accurate digital data from a scan that provides the public a useful alternative to what is already in the market.

Reference to any prior art in the specification is not an acknowledgement or suggestion that this prior art forms part of the common general knowledge in any jurisdiction or that this prior art could reasonably be expected to be combined with any other piece of prior art by a skilled person in the art.

SUMMARY

In a first aspect, the present invention provides an apparatus for facilitating the acquisition of a scan during an intraoral scanning procedure using an intraoral scanner, including: an elongate body having an attachment portion configured to attach the elongate body with an implant in a patient's mouth, the implant having a longitudinal axis, whereby the elongate body is adapted to extend substantially perpendicular to the longitudinal axis of the implant when mounted to the implant; the elongate body having a substantially planar upper surface and one or more side walls extending downwardly away from the upper surface; wherein the upper surface and the one or more side walls are observable in a resulting scan when the intraoral scanner scans the apparatus in a direction perpendicular to the upper surface(s).

At least in preferred embodiments, the apparatus of the present invention can be used to establish an extremely accurate three-dimensional frame of reference for use in the design of dental prosthetics.

In other words, the present invention is advantageously designed to allow a user to obtain more accurate scan information from digital implant impressions (i.e. from intraoral scanning) for a range of implant cases, including fully edentulous cases where the implants are distributed throughout the full arch of a patient's mouth. The user can accurately model the position and orientation of the implant(s) inserted into the patient's mouth, thereby allowing for more accurate digital implant positional capture and digital design of prosthetic appliances for the patient that utilise the implant location information. These benefits are achieved because of the unique design of the surfaces of the elongate body of the apparatus. Having the upper surface(s) and at least one or more side walls observable in a resulting scan when the intraoral scanner scans the apparatus in a direction substantially perpendicular to the upper surface, an operator needs only to move the head of the scanner within a limited range of movement, i.e. lingual-labial direction, mesial-distal direction, upward-downward (vertical) direction, rather than the conventional five axes of movement most current scanning procedures require. The extra axes of movement of the head of the scanner during the scanning procedure (i.e. through rotational movement) can introduce significant sources of error when the scans are utilised during the post-processing stage.

During the post-processing stage, the upper surface(s) and the one or more side walls observable in the scan are used as references that can be ultimately compared with stored information contained within a library on a computer, the stored information including precise models and measurements of the apparatus. From this, the known measurements of the apparatus can be assigned to the scan, thereby allowing the location and orientation of the implants relative to the soft tissue of the patient's mouth to be accurately determined. Having this information in a digital model allows for the digital design of a best-fit implant framework, for example, a partial or full arch implant bar, whereby the determined location and orientation of the implant(s) can be used to define suitable fixing positions of the implant framework, the framework also fitting the soft tissue of the arch.

In an embodiment, the one or more side walls surround all or a substantial portion of the periphery of the upper surface, all being viewable from above the upper surface. The benefit of such an arrangement is that the apparatus provides a plurality of reference points and surfaces around the upper surface that can be used in the post-processing steps discussed above and in greater detail below. For example, separate scans of the apparatus can be taken during the intraoral scanning procedure and then aligned with one another during the post-processing stage using the reference points and surfaces situated around the periphery of the upper surface, along with the upper surface itself. This provides for more accurate alignment between scans, and greater confidence in the accuracy of the scans when the precise measurements of the location and the orientation of the implant(s) are determined.

In an embodiment, the upper surface and a lower surface of the elongate body define elongated hexagons, each with its elongated sides extending substantially in parallel from a first end to a second end. The pair of shorter hexagonal sides at the first end of both the upper surface and the lower surface may be longer in length relative to the pair of shorter hexagonal sides at the second end of both the upper surface and the lower surface. These faces may therefore define a relatively acute angle between the pair of sides at the first end, whereas they meet at a larger, relatively obtuse angle at the second end. These faces may therefore be of substantially trapezoidal shape.

In an embodiment, the one or more side walls taper inwardly towards the upper surface of the elongate body, thus providing a sloped skirt depending from the upper surface. The angle of this tapering may be selected as desired for best results. Ideally, each of the one or more side walls is substantially planar. Alternatively, one or more of the side wall(s) may be of curved form. Preferably, a plurality of side walls, defining a plurality of interconnected facets, is provided, each facet observable by the intraoral scanner when scanning in a direction substantially perpendicular to the upper surface.

By way of particular example, the facets may be substantially planar and inclined from the direction perpendicular to the upper surface by an angle between about 15° and about 40°, preferably around 25°.

In one embodiment, the elongate body includes a first end and a second end, both ends having generally pointed end shapings, each defined by two meeting facets. This has the advantage that, when used in conjunction with other adjacent apparatus, shadowing or obscuring of one apparatus by another can be minimised.

In one embodiment, the apparatus includes a fiducial marker mounted to or integral with the upper surface. The incorporation of the fiducial marker can assist in the alignment between separate scans because the marker acts as a further point of reference for accurately aligning the scanned apparatus, particularly for alignment in the vertical direction. This is because the marker has known dimensions and is provided in a known position and orientation relative to the elongate body. The fiducial marker provides an additional source of 3-D information in the scan data capture that can be used for vertical corrections between scans that may be required during the post-processing stage.

The fiducial marker may be of any suitable shape. In one form, the fiducial marker is spherical, but other shapes such as triangular, square, conical, cylindrical, oval, etc. may be used. The fiducial marker may be mounted to the upper surface of the elongate body in any suitable manner. Alternatively, the fiducial marker may be integral with the upper surface by either manufacturing the fiducial marker with the elongate body as one integrally formed component, or by permanently fixing the fiducial marker to the elongate body, such as by welding or other suitable process.

In an embodiment, the attachment portion may be configured to receive a fastening element, such as a prosthetic screw, in order to fixedly attach the elongate body to an implant in the patient's mouth (or to some other intermediate component(s) between the implant and the elongate body). The apparatus may then be removable from the implant (eg. following unscrewing the prosthetic screw) once the scanning is complete.

In an embodiment, the upper surface of the elongate body includes an aperture or recess configured to receive an indicator element that is identifiable in a resulting scan. The recess may be provided by a bore through the elongate body, the bore serving the engagement of the elongate body with the implant. The indicator element may be in the form of a plug, configured to be retained in the recess when the apparatus is being scanned. This can be useful during post-processing, as the indicator element can be used to identify a characteristic of the apparatus or of the scan. For example, if a plurality of apparatus are being scanned (for example as part of the scanning of a full arch), the element may be placed in the recess of the first apparatus to be scanned, thereby indicating the starting position of the scan path. Such information can assist in conveying information about the scanning path. This information can be important as generally the scan data of an apparatus scanned at the beginning of a scan path will be more accurate than that of an apparatus scanned towards the end of the scan path.

In one embodiment, one or more side walls adjacent the attachment portion include at least one cut-out portion configured to enable the scanner to retrieve data to assist in defining the longitudinal axis of the implant. The cut-out portion(s) preferably extend towards the attachment portion, thereby enabling visualisation of a surface of the attachment portion beneath the elongate body. For example, the cut-out portion(s), when viewed from the direction perpendicular to the upper surface by the scanner, enable a view of a convex surface associated with a bore of the attachment portion, which is to be attached to the implant. This additional information provided by virtue of the cut-out portion(s) can be used during post-processing to assist in correcting any scan discrepancies (such as x-y scan data) along the z-axis that could arise in a resulting scan. Further advantages arise based on the nature of conventional intraoral scans and the resulting post-processing. The cut-out portion(s) can act as a smooth transition path that joins surfaces created by the scanner by connecting the observable surfaces of the apparatus and surfaces of underlying tissue as a complete scan. This is achieved without the need to tilt the head of the scanner in a direction perpendicular with the longitudinal axis of the implant in the way conventional scan apparatus require. It is this tilting or rotation of the head of the scanner that can introduce inaccuracies in the resulting scan. The joining of surfaces between the apparatus and the underlying tissue also mitigates the tendency of most post-processing software to treat separated or inconsistent scan data as noise, which in some cases results in automatic deletion of this data.

Preferably, there are at least two cut-out portions, with at least one located on a posterior side of the apparatus and at least one located on an anterior side of the apparatus.

In one embodiment, one or more of the upper surface and side walls include an identifier which enables identification of the apparatus in a resulting scan. Preferably, the identifier is provided on the upper surface. The identifier may be of any suitable form, such as one or more projections, one or more recesses, a scannable medium (e.g. barcode), etc. The identifier can convey different types of information about the apparatus, such as height, length, width or dimensional tolerance, etc. This is particularly important when the apparatus is used in conjunction with other similar apparatus as part of a scanning procedure.

In a second aspect, the present invention provides a method of performing an intraoral scanning procedure, including inserting one or more implants into a patient's jaw, each of the one or more implants having a longitudinal axis, mounting the above-defined apparatus to the one or more implants in the patient's mouth, and scanning the apparatus and at least a part of the soft tissue in the patient's mouth, thereby producing a set of scan data for use in determining the relative position and orientation of the one or more implants relative to the soft tissue.

In one embodiment, the method may further include selecting one or more modular forms of said apparatus from a plurality of different modular forms of the apparatus, in order to best fit a space to be scanned in the patient's mouth.

In another embodiment, where a plurality of implants are inserted into the patient's jaw, the method further includes mounting each apparatus to its respective implant in a way resulting in a substantial elongate overlap transition from each apparatus to each adjacent apparatus, across the space to be scanned.

It will be appreciated that the second aspect of the invention can include any of the features defined with respect to the first aspect of the invention.

In a third aspect, the present invention provides a kit including a plurality of items of the above-defined apparatus, including items of different dimensions to each other, such that a plurality of items may be selected for a particular patient's mouth in accordance with the area of the patient's mouth to be scanned and/or in accordance with relative positions of one or more existing implants.

The different dimensions can include different lengths and/or heights. Different heights can be provided to accommodate the depth of a given implant relative to the surrounding tissue. For example, undue pressure exerted by the tissue on the underside of one item can be avoided by using an item with a greater height. Further, an item of suitable height can be used to ensure the depth of field of the scanner head is closer to the tissue, without touching the tissue, thereby improving accuracy of the scan and hence better stitching between the scan data. In a similar fashion, different lengths can be provided to accommodate different distances between implants.

In one embodiment, each unique item in the kit is measured and the measurements are stored in a digital library for post-processing of a resulting scan.

It will be appreciated that the third aspect of the invention can include any of the features defined with respect to the first or second aspect of the invention.

In a fourth aspect, the present invention provides a method of performing an intraoral scanning procedure for determining the position and orientation of one or more implants in a patient's mouth, each implant having a longitudinal axis, the method using one or more scannable bodies and including providing a scannable body on each of the one or more implants, the scannable body extending substantially perpendicular to the longitudinal axis of the respective implant, the scannable body having a substantially planar first surface facing in a direction away from the soft tissue of the patient's mouth, and one or more further surfaces extending from the first surface, wherein the one or more further surfaces are viewable from a direction perpendicular to the first surface, scanning the one or more scannable bodies, thereby producing a set of scan data associated with the intraoral scanning procedure, and assigning information from a set of stored data to the scan data, and determining from the scan data and the assigned information the position and orientation of the one or more implants.

It will be appreciated that the fourth aspect of the invention can include any of the features defined with respect to the first, second, and third aspects of the invention.

As used herein and except where the context requires otherwise, the term "comprise" and variations of the term, such as "comprising", "comprises" and "comprised", are not intended to exclude further additions, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
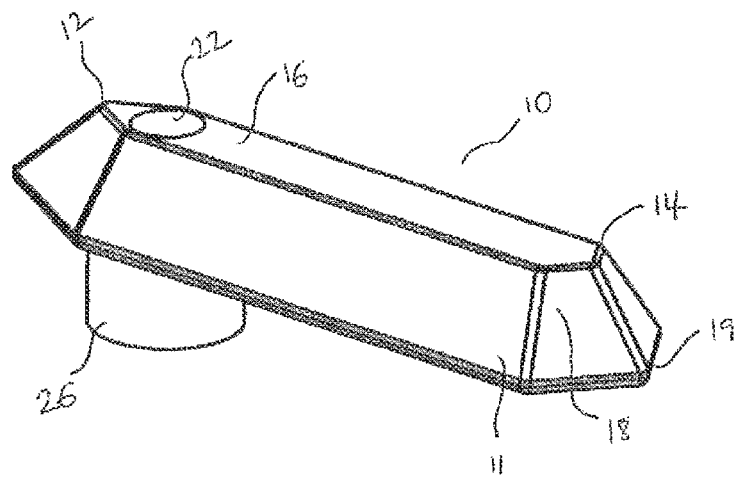
FIG. 1 illustrates a perspective view of an apparatus according to an embodiment of the present invention.
Figure 2:
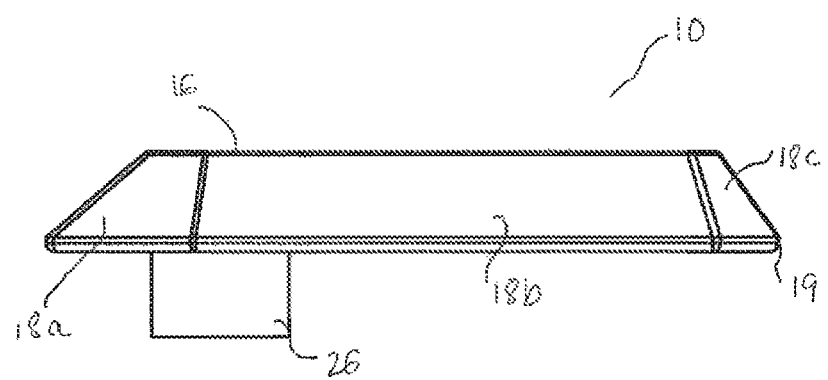
FIG. 2 illustrates a front elevation view of the apparatus of FIG. 1.

It will be understood that the invention disclosed and defined in this specification extends to all alternative combinations of two or more of the individual features mentioned or evident from the text or drawings. All of these different combinations constitute various alternative aspects of the invention.

Reference is made to FIGS. 1 to 5 which illustrate in various views an embodiment of the apparatus of the invention. A scan abutment (or scan gauge) 10 is configured to be attached directly or indirectly to an implant in a patient's mouth, eg. an implant pin (ie. dental implant) surgically implanted to the patient's mandible or maxilla. In some examples, scan abutment 10 can be attached to an intermediate adaptor (not shown) such as a multi-unit adaptor (as known in the art), which is attached to the implant. It will be noted that references to the implant can include (where the context permits) reference to the intermediate adaptor.

References herein to a vertical direction refers to the vertical direction as generally understood in the anatomical position (i.e. patient upright). References herein to upper and lower are to be understood in relation to the scan abutment as viewed in the accompanying drawings. However, as will be understood, depending on whether the scan abutments are used in the upper or lower arch of the patient's mouth (ie. with a maxillary or mandibular implant, respectively), the terms upper and lower may be reversed. In the depicted embodiment, the scan abutments are used in the lower arch of the patient's mouth (ie. attached to mandibular implants), so the terms 'upper' and 'lower' will be used from that viewpoint.

The scan abutment 10 includes an elongate prismatic body 11 having a first end 12 and a second end 14. Body 11 is preferably a solid body, but can instead be a hollow body. Body 11 further includes a planar upper surface 16, a planar lower surface 17 and a plurality of side walls 18 extending between the peripheral edges of the upper surface 16 and the peripheral edges of the lower surface 17. As can be seen, the upper and lower surfaces 16, 17 are in the form of similarly shaped elongated hexagons, each with its elongated sides extending in parallel from the first end 12 to the second end 14. The pair of shorter hexagonal sides at the first end 12 of both the upper surface 16 and the lower surface 17 are longer in length relative to the pair of shorter hexagonal sides at the second end 14 of both the upper surface 16 and the lower surface 17. These faces therefore define a relatively sharp, acute angle between the pair of sides at the first end 12, whereas they meet at a larger, obtuse angle at the second end 14. This difference in morphology arises from a need to minimise lateral overlap (and the creation of associated shadowing) which can adversely impact on scanning accuracy.

Prismatic body 11 therefore has the form of a stretched hexagonal frusto-pyramid, with a single plane of symmetry running along the longitudinal centreline.

It will be appreciated by a person skilled in the art that the upper surface 16 and lower surface 17 need not necessarily have the same shape as depicted in this embodiment, but can take on any other suitable shape such as rectangular, oval, triangular, polygon, etc. However as will be evident from the discussion below, a series of straight edges and associated planar side wall facets are preferred. Further, the overall shape of the body 11 does not necessarily require the upper surface 16 and the lower surface 17 to have the same shape, with variations in the overall shape to that shown in the present embodiment also possible.

The side walls 18 include a number of distinct facets, in the depicted example six facets 18a-18f, that extend between the respective edges of the upper surface 16 and the lower surface 17 around the whole periphery thereof. The peripheral edge of the lower surface 17 includes a chamfered transition lip 19, from which facets 18a-f extend upwardly towards upper surface 16. As can be seen in the figures, the facets 18a-f generally taper inwardly from the chamfered transition lip 19 to the upper surface 16, thereby defining a series of interconnected planar sloped walls. The slope of the side walls 18a-f can be selected as desired. Ideally, this slope is between 15° and 40° to the vertical (ie. the direction perpendicular to upper surface 16), and is preferably around 25° to the vertical. In other embodiments, the side walls may be curved, or a single curved side wall may extend from and surround the entire upper surface 16. However, preferably, for ready surface identification and data manipulation, planar facets are preferred.

Figure 3:
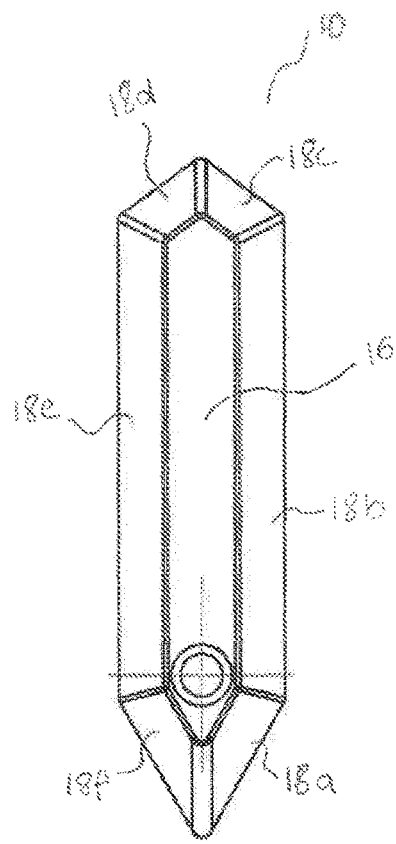
FIG. 3 illustrates a plan view of the apparatus of FIG. 1.
Figure 4:
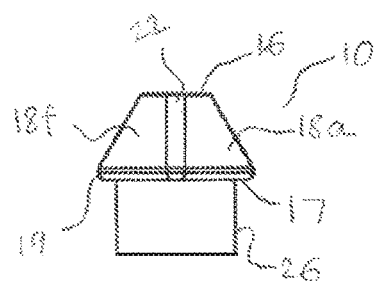
FIG. 4 illustrates a side elevation view of the apparatus of FIG. 1.
Figure 5:
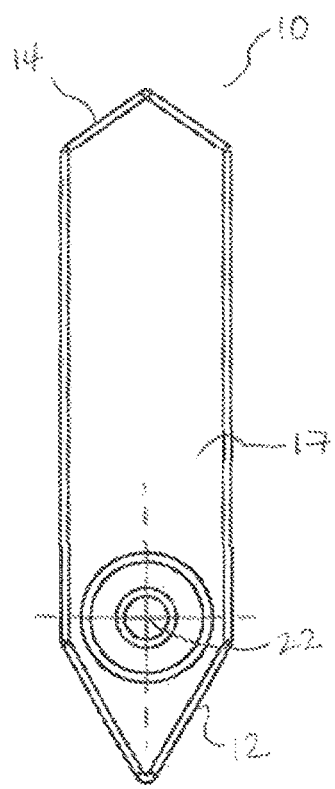
FIG. 5 illustrates a bottom plan view of the apparatus of FIG. 1.

Significantly, when the scan abutment 10 is viewed by the scanning head of an intraoral scanner in a direction substantially above and perpendicular to the upper surface 16 (with scan abutment 10 mounted to the proximal end of an implant in the patient's mouth), the six facets 18a-18f and the upper surface 16 are all directly observable in the scan (as illustrated in the plan view of FIG. 3). In this way, all seven facets can act as reference surfaces when aligning separate scans taken of the scan abutments 10 within the patient's mouth. This provides full 3-D reference information concerning the relative position and orientation of the scan abutment, and thus the position and orientation of the implant relative to the soft tissue in that area of the patient's mouth.

This is of significant benefit, as the scan operator need only manoeuvre the scan head in a limited range of movement within the patient's mouth, i.e. lingual-labial direction, mesial-distal direction, and—as necessary—the vertical direction. Manoeuvring the scan head in these directions will capture the upper surface 16 and the side walls 18 without the need for the scan head to be manoeuvred in any rotational directions. This is important because rotational movements of the scan are found to provide the greatest source of potential error in capturing internal scan data. This is generally related to the internal knitting algorithms that interpolate any gaps present in the image data, which can result in significant distortion of the overall scan and thus inaccuracy. It is of course nearly impossible to eliminate some rotational movement from occurring during the scanning procedure and to eliminating at least some instances of the scanner software being required to stitch together gaps in the scan image. However, by eliminating the need for substantial rotation of the scan head during the scanning procedure, the operator can largely maintain movement of the scan head in only the limited range of movement discussed above, severely limiting the amount of data knitting required.

As noted above, from the lower surface 17 extends chamfered transition lip 19. The transition lip 19 provides that the scan abutment 10 has a relatively sharp lower edge detail to side walls 18. This assists in reducing the risk of tissue overlap of the lower portions of the side walls 18. The lower edge detail also assists in more precisely defining the implant/tissue boundary. This can improve scan accuracy by minimising interpolation errors that can arise, for example when tissue is mistaken for implant.

Whilst it is advantageous for the scan abutments 10 to include side walls that are visible around the whole periphery surrounding the upper surface 16, this need not be the case. For example, having side walls that are visible around only a portion of the periphery of upper surface 16 can still provide sufficient reference surfaces for use in providing a suitable data set and in comparing and aligning separate scans of the scan abutments 10. However, it will be apparent to a person skilled in the art that the more points and facets of reference that are visible, the greater the accuracy and usefulness of the scan.

As can be seen from the overall shape and configuration of the scan abutment 10, the first end 12 and the second end 14 of the scan abutment 10 terminate in pointed ends, provided by the meeting of facets 18a; 18f and 18c; 18d, respectively. The benefit that arises from using scan abutments with these pointed ends is best appreciated in scenarios where multiple scan bodies are placed in the mouth of the patient (for example, when scanning a full or partial arch). In a preferred scanning procedure, scan abutments 10 are placed adjacent one another in order to take the most accurate scan of the desired scanning region. Having the scan abutments in close proximity means that if the ends of the scan abutments were, for example, curved, some of the surfaces of the side walls may be obscured by a directly adjacent scan abutment, thus limiting the detail available for the post-processing stage. Having relatively pointed ends reduces the likelihood of such overlap when the scan abutments are in close proximity.

The elongate body 11 includes a bore 22 extending between the upper surface 16 and the lower surface 17, adjacent the first end 12. The bore 22 is configured to accommodate the proximal end of an implant (or intermediate adaptor) and to receive a prosthetic screw to secure the scan abutment 10 to the implant. Extending vertically from the lower surface 17 is a cylindrical attachment portion 26 configured to sit over the implant when the scan abutment 10 is attached thereto. In some embodiments, the implant or suitably attached intermediate adaptor can provide a male connection portion complementarily shaped to fit within bore 22, with the lower end of the attachment portion 26 resting upon a planar lower surface of the implant or adaptor. The male connection portion may be in the form of a cylindrical cap that permits a snug fit between the bore and male connection portion.

Whilst the depicted embodiment provides for a screw connection between the scan abutment 10 and the implant, other means of connecting the scan abutment 10 with the implant are also possible. For example, the scan abutments may include internal threading that can be mated with the implant bearing corresponding threading external, or bore 22 may connect to the proximal head of the implant in a snap-fit arrangement.

Bore 22 may serve an additional function to receive an indicator element that can convey additional information in a scan. In one embodiment, the indicator element is in the form of a plug (not shown) that fits within and covers the upper end of bore 22. The indicator element may, for example, be used to indicate the direction in which a scan has been taken. For example, if the scan is taken of a plurality of scan abutments from left to right, the indicator element may be placed on the left-most scan abutment, providing an indication in the scan data that the left-most scan abutment was scanned first.

Recording the direction of a scan in this way can be particularly helpful as, ordinarily, when the scan head travels from the start to the end of a scan path, the information provided at the start of the path is likely to be more accurate than that provided towards the end of the path. This difference in accuracy arises from errors that accumulate as the scan head traverses a scan path from start to finish. Errors are minimised by overlapping the left-to-right scan with the right-to-left scan using the perpendicular lengths of several markers. This yields a combination of several scans that can be suitably grouped together and used to assist in weighting the acquired image data. However, as will be understood, the indicator element could be used in any other way that can convey suitable information in the resulting scan to the end user.

In one embodiment, the scan abutment 10 includes a fiducial marker (not shown) mounted to or integral with the elongate body 11. The fiducial marker is preferably in the form of a three-dimensional shape such as a sphere, prism, etc. The fiducial marker is of known dimensions and known position/orientation relative to scan abutment 10, thus providing further 3D reference information that can be used in the post-processing steps of aligning separate scans, particularly for alignment in the vertical direction.

The scan abutments 10 can be provided to an operator as a kit 1000 (illustrated in FIG. 11) with an assortment of elements of different dimensions that can be selected by the operator to suit the size and shape of the patient's mouth, so to provide the amount of coverage required for the scan procedure. In most cases, a plurality of scan abutments 10 will be used to span the space between multiple implants inserted in the patient's mouth, each scan abutment 10 attached to a separate implant. As will be understood, greater flexibility is provided by having scan abutments of different dimensions. For example, suitable dimensions for the scan abutments 10 can include an overall length ranging from about 10 mm to about 30 mm, and overall heights (ie. viewed in elevation) ranging from about 3 mm to about 10 mm. However, these dimensions are only exemplary, as a scan abutment can be manufactured to any suitable size.

The scan abutments 10 are typically fabricated from Titanium Grade 5. However, other suitable materials may be used, such as an alternative suitable metal or a plastics material.

Scan abutments 10 are generally designed in CAD/CAM software and then manufactured on suitable 5-axis CNC machines. As the precision of the manufactured scan abutments is critical for the scanning procedure, after the manufacture of each scan abutment, a coordinate measuring machine (CMM) is used to precisely measure all the relevant dimensions of the scan abutment. This information is stored on a database so that it can be called upon during the assignment step in the method, as described in detail below. Hence each individual kit can also include its own unique digital library, with precise measurements of each scan abutment 10 of the kit stored in the library. The digital library for each kit of scan abutments will thus be unique to that kit. A kit identifier (such as a kit number) can be assigned to each kit and therefore to each scan abutment within the kit. This ensures that the assignment step of the method described below produces the most accurate representation of the scan bodies and hence the precise positions of the implants (as well as the other scanned data points) in a patient's mouth.

An exemplary method of using the scan abutments 10 will now be described, in particular as part of a scanning procedure for a full arch of an edentulous patient. However, a person skilled in the art will appreciate that a similar method can be applied when scanning a portion of the full arch. The exemplary method includes providing a plurality of implants within the mouth of a patient, being screwed pins fixed into the maxillary or mandibular bone in a conventional surgical procedure. The suitable number and positioning of the implants will depend on the particular circumstances and the prosthesis required. Generally, to support a fixed complete prosthesis in the maxilla, four implants provide sufficiently high predictability, with clinicians often placing six implants. Whilst it may be ideal in many cases for the implants to be placed parallel to one another, due to surgical or structural limitations this is often not achieved.

A plurality of scan abutments are then provided, each attached to the proximal head of an implant. This attachment is achieved by engaging the bore 22 of the scan abutment 10 over the head of the implant and attaching thereto by a prosthetic screw accessed from the upper end of the bore. The scan abutments 10 are selected and positioned to substantially cover the full area of the arch, with an example implementation shown in FIG. 6. The scan abutments should be positioned in proximity to each other, but they do not need to touch and it is considered preferable to have an overlap transition from around the midpoint of one abutment to the midpoint of the next (when viewed in elevation—see FIG. 6). This is to minimise and simplify the stitching of the scanned data (thus reducing potential for errors to arise in the data post-processing) and to ensure that two or more known surfaces (facets) belonging to adjacent scan abutments 10 are visible in the scanner field of view when moving between the scan abutments.

Figure 6:
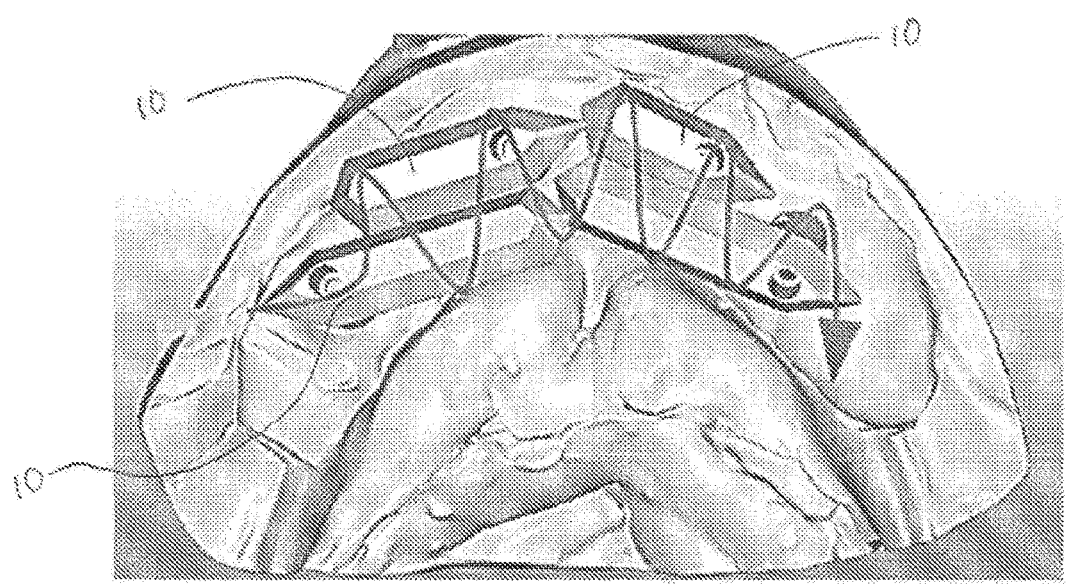
FIG. 6 illustrates a plan view of a plurality of apparatus according to an embodiment of the present invention inserted into the mouth of a patient.

As will be understood, the implementation shown in FIG. 6 is only one example of positioning the scan abutments. Care should be taken when arranging the scan abutments so that most and preferably all of the upper surfaces and side walls of the scan abutment will be visible from above (and thus to the scanner head). Care should also be taken to avoid significant gaps between adjacent scan abutments as much as possible, as these gaps can provide sources of error. Further, a head-to-tail arrangement of the scan abutments as shown in FIG. 6 is considered preferable for acquiring maximum information and minimising sources of error.

Once the scan abutments are in place, the operator begins the intraoral scanning procedure using a conventional intraoral scanner. The practitioner may first place an indicator element in the bore 22 of a selected scan abutment, so as to provide an indication of which scan abutment was the first scanned during the procedure. The operator will then begin to scan from one end of the arch to the other, preferably maneuvering the scanner in a generally zig-zag path as shown in FIG. 6. As will be understood, the operator will only need to manoeuvre the scan head in a limited range of movements (as discussed above), avoiding the need for any rotational movement of the scan head. Preferably, the operator will then scan the scan abutments along the opposite direction to the initial scan (i.e. from right to left), to generate a second data set. For improved accuracy, further scans in both directions can be performed by the operator so that the multiple scans can be utilised in the post-processing stages. In addition, the operator takes scans of the same portion of the patient's mouth with the implants in place but without the scan abutments, in order to acquire full impression information regarding the soft tissue. This can be done before or after the scan abutments are in place. Further, scans can be taken before implants are installed in the mouth, although this is not considered essential due to the slight differences that can be created by the implant placement surgery. Each set of scan data takes the form of an STL file containing raw point cloud data.

Figure 7:
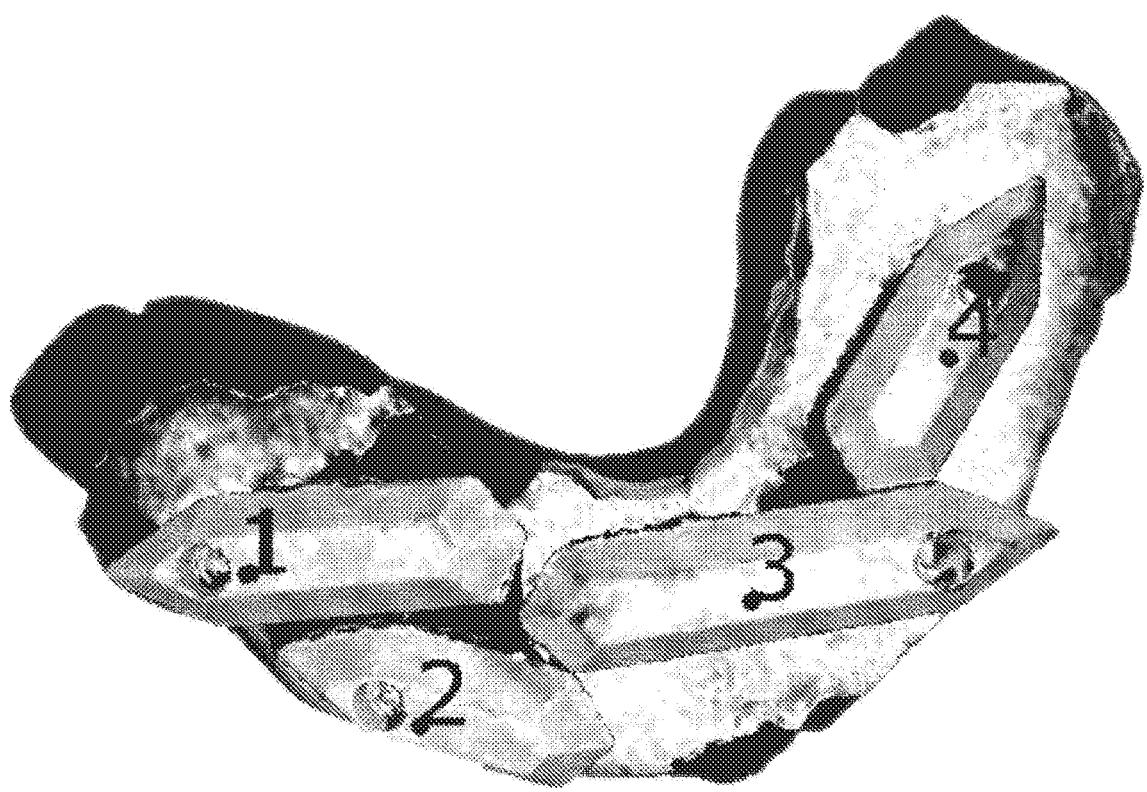
FIG. 7 illustrates an example of resulting scans in software during a post-processing step in a method in accordance with an embodiment of the present invention.

This scan data is then passed to post-processing. As part of the post-processing stage, the received STL files which contain the separate scans of the arch with the scan abutments are compared and aligned with one another. One example of this process is shown in FIG. 7, where using computer software the sets of scan data of the various scans are aligned with one another and the discrepancies between the respective scans highlighted. For example, if during this alignment stage the discrepancies between the respective scans is in excess of 50 μm, the inaccurate scan may be omitted from the alignment process. The alignment process provides a measure as to how well each of the scan abutments align between the separate scans.

Each scan abutment can be appropriately aligned in each scan using the known key surfaces (the upper surface and the side walls). Ideally, all seven facets of scan abutments are used. However, if one or more of the key surfaces may be determined to be inaccurate it can be omitted from further processing. This can be due to being obscured in the scan in some way, or to an inaccuracy that has arisen in the scan which has prevented the surface from being aligned with the corresponding surface in another scan. This will be apparent if the surface of the scan abutment has a discrepancy relative to the other scans that is higher than an allowable threshold (such as a facet deviation between scans larger than 10 microns). In such circumstances, this surface or these surfaces may be omitted from consideration during the alignment stage and only the more accurately aligned surfaces taken into account in an averaging process between the (non-rejected) information from the different scans. In processing the data, if there is a scaling error from one scan to another, then the actual marker measurements can be used to re-scale up or down to allow accurate comparison of data sets.

Once the alignment process has been completed to a satisfactory level, the scan abutments can be separated in the software from the rest of the scanned elements (the soft tissue information), and a file of the now averaged scan saved for use in the subsequent steps. The stored digital files of the respective scan abutments can now be accessed and used to assign the exact measurements of the respective scan abutments to the averaged scan. The accurate dimensions for each facet of the scan body are assigned to the averaged scan and from this the precise positioning and orientation of each of the implants are determined, relative to the precise form of the soft tissue. This information, in combination with the scan taken without the scan bodies (showing all the underlying soft tissue) allows an end user to digitally construct an implant framework for mounting to the implants by using the position and orientation of the implants as the corresponding mounting points of the implant framework. In addition, peripheral soft tissue data captured in the scan body can be matched with the underlying soft tissue scan in order to identify structures common to the two scans. In turn, these identified common structures can be used in operations such as merging multiple scans.

It will be appreciated that other information may be required to ultimately construct a dental prosthesis for a patient who has not previously had a dental prosthesis. The reader is directed to Applicant's earlier application PCT/AU2020/050215 (the contents of which are incorporated herein by reference) for information relating to the taking of impressions of the patient's mouth.

It will also be appreciated that a similar method can be applied in circumstances where a new prosthesis is to be manufactured for a patient having a pre-existing prosthesis, and therefore implants already inserted in the patient's mouth. It is relatively common for pre-existing prosthesis to become worn or damaged over time, and there can be great challenges in manufacturing a suitable replacement prosthesis for the patient. However, this process can be simplified substantially by the present invention.

A number of additional steps relative to the above described methodology can be employed in such circumstances. In a first step, a scan of the existing prosthesis (e.g. an upper arch) in-situ is acquired. This is then followed by acquiring a scan of the opposing arch. A full bite scan can then be acquired, the bite scan providing information relating to both the upper and lower arches. In a next step, the pre-existing prosthesis is removed. Once removed, the implants (or intermediate adaptor) are now visible. Depending on the spacing between the existing implants, scan abutments 10 of suitable dimension (in accordance with the purpose described above) are selected and fixed to the implants. In a similar manner to that described above, the scan abutments 10 are scanned, and a further scan is taken of the underlying tissue with the scan abutments 10 removed.

Figure 11:
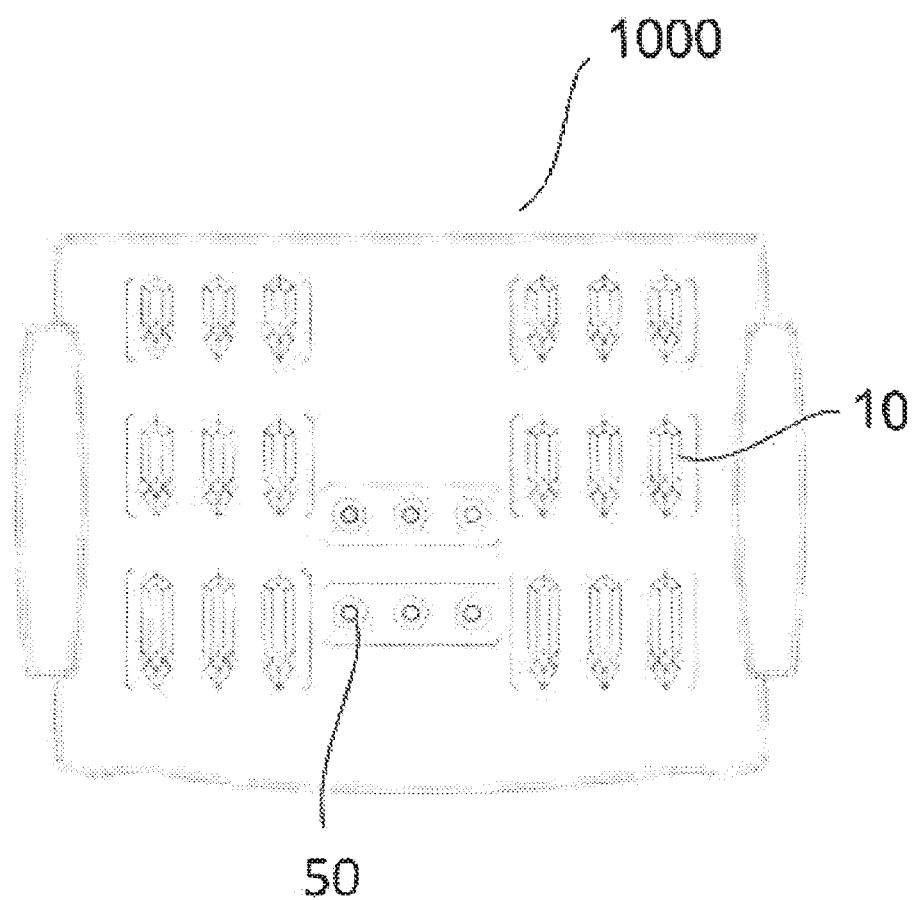
FIG. 11 illustrates a kit including a plurality of apparatus of different dimensions in accordance with an embodiment of the invention.

In the present example, given that there already exists a pre-existing prosthesis, the information provided by the existing prosthesis can simplify the post-processing and teeth design stage. Thus, the present method includes acquiring a 360° scan of the existing prosthesis outside of the mouth. To assist with alignment of the scans during post-processing, cylindrical caps 50 (included in the kit, as shown in FIG. 11) of known dimension can be attached to fixing formations on the existing prosthesis before the scan is taken. These caps 50 effectively simulate the precise location of the implants (or intermediate adaptors) and therefore provide a geometric shape of known dimension that are fully visible in the scan. This scan can be used with the acquired scan of the scan abutments to generate an accurate model of the location of the implants in the patient's mouth. Combined with the scan of the patient's tissue, an accurate representation of the overall mouth of the patient is provided which allows for design of a new dental prosthesis, such as prosthesis described in the Applicant's prior application PCT/AU2019/051222, the contents of which are incorporated herein by reference.

As noted above, caps 50 can be provided along with scan abutments 10 as part of kit 1000.

Figure 8:
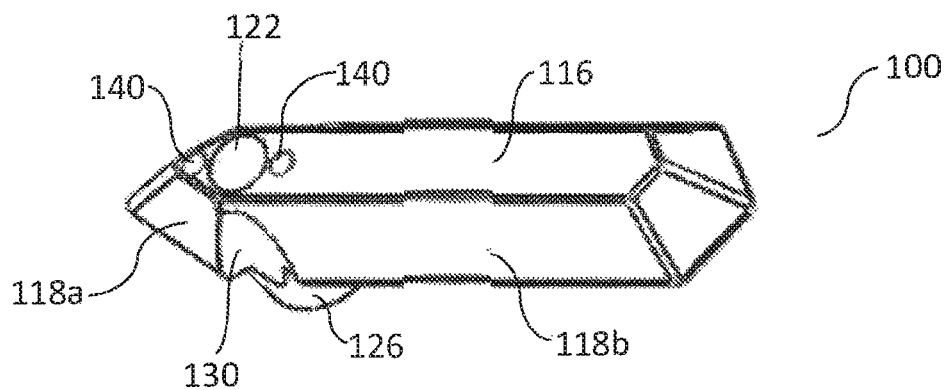
FIG. 8 illustrates an upper perspective view of an apparatus in accordance with another embodiment of the invention.
Figure 9:
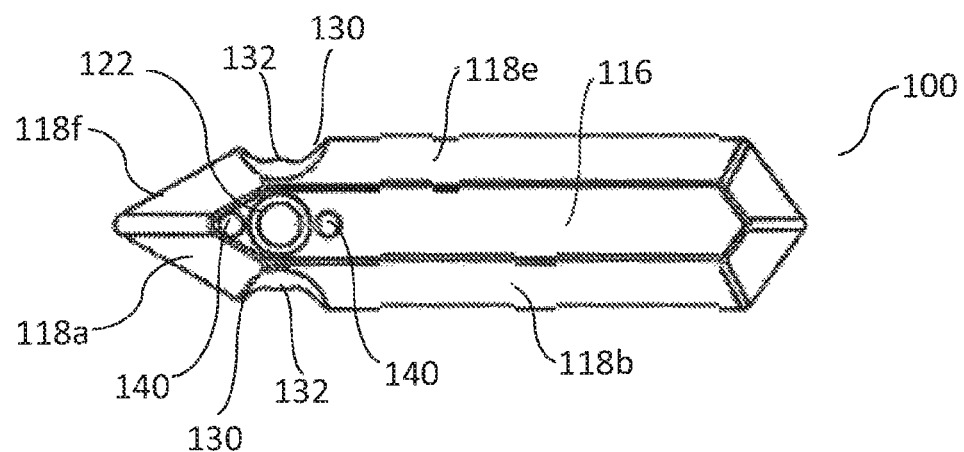
FIG. 9 illustrates a plan view of the apparatus of FIG. 8.
Figure 10:
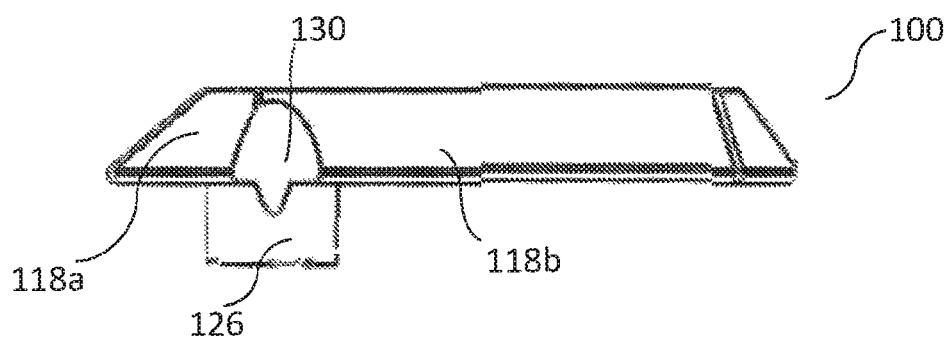
FIG. 10 illustrates a front elevation view of the apparatus of FIG. 8.

Reference is now made to FIGS. 8-10, which depict a slightly modified form of scan abutment 100. Scan abutment 100 includes several common features to scan abutment 10, and therefore these features will not be described in any detail again. Common features between scan abutment 10 and scan abutment 100 will be provided with a '100' series reference numeral when referencing scan abutment 100.

In addition to the features described with reference to scan abutment 10, scan abutment 100 includes part-cylindrical cut-out portions 130 provided in opposed side walls adjacent bore 122. In the depicted example, two cut-out portions 130 are provided, one in side wall 118*e* and one in side walls 118*b*, as shown in FIG. 9. As will be best appreciated from the figures, the cut-out portions 130 enable direct visualisation, when viewed from above, of part of outer surfaces 132 of the attachment portion 126 around concentric bore 122. As attachment portion 126 sits over the implant when the scan abutment 100 is attached thereto (aligned with the longitudinal centreline of the implant), visual access to surfaces 132 enables the scanner to acquire additional data along the longitudinal axis of the implant. This additional information can assist during post-processing to correct any vertical direction discrepancies that may otherwise arise from the scan, as well as provide further information of the location of the implant relative to the underlying tissue.

Related to this, the outer surfaces 132 of attachment portion 126 act as a smooth transition path between scanned data representing the observable surfaces of the scan abutment 100 and surface features of the underlying tissue. This is achievable without the need to tilt the head of the scanner in a direction perpendicular with the longitudinal axis of the implant so to view the surfaces of attachment portion 126.

The contiguous scan information in the transition from scan abutment 100 to the underlying tissue can significantly mitigate the risk, inherent in conventional post-processing software, that physically separated or otherwise mutually inconsistent scan data is treated as noise and is automatically deleted from the dataset.

Cut-out portions 130 may be formed by a milling step undertaken during manufacture of scan abutment 100. Alternatively, cut-out portions 130 may be formed by other manufacturing methods, such as provided as recessed portions in a casting of the scan abutment.

Scan abutment 100 further includes an identifier marking, shown as a pair of circular recesses 140 formed in the upper surface 116, on opposite sides of bore 122. The identifier markings are intended to be visible in the resulting scan and provide dimensional and tolerance information concerning the given scan abutment 100. These markings are useful during the assigning step of the above described method in order to indicate which scan abutment (from a plurality of scan abutments) has been used.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A scan gauge for facilitating acquisition of a scan during an intraoral scanning procedure in a patient's mouth, comprising:
   an elongate body having an upper surface, a lower surface, and a plurality of side walls extending between peripheral edges of the upper surface and peripheral edges of the lower surface, wherein one or more of the plurality of side walls slope outwardly from the upper surface to the lower surface of the elongate body so that the upper surface and the one or more sloped side walls are observable in an intraoral scan when the scan gauge is scanned from substantially above and perpendicular to the upper surface; and
   an attachment portion arranged on a lower surface of the elongate body, whereby the elongate body extends substantially perpendicular to a longitudinal axis of the attachment portion, and is configured to receive a fastening element to attach the elongate body to an implant or to an intermediate component in the patient's mouth,
   wherein one or more of the plurality of side walls include at least one cut-out portion configured to enable an intraoral scanner to retrieve data from a surface of the attachment portion when the scan gauge is scanned from substantially above and perpendicular to the upper surface of the elongate body, and
   wherein the elongate body comprises one or more identifier markings on the upper surface of the elongate body or on one or more of the sloped side walls, or on both the upper surface and on one or more of the sloped side walls, wherein the identifier markings are arranged to be observable in an intraoral scan when the scan gauge is scanned from substantially above and perpendicular to the upper surface of the elongate body to provide dimensional information, tolerance information, or both dimensional and tolerance information for the elongate body.

2. The scan gauge of claim 1, wherein the at least one cut-out portion extends towards the attachment portion, thereby enabling intraoral scanning of a surface of the attachment portion when the scan gauge is scanned from substantially above and perpendicular to the upper surface of the elongate body.

3. The scan gauge of claim 1, wherein the attachment portion comprises a bore that is complementarily shaped to fit a male connection portion of an implant or intermediate adapter.

4. The scan gauge of claim 3, wherein the male connection portion comprises a cylindrical cap that fits into the bore.

5. The scan gauge of claim 1, wherein the fastening element comprises a prosthetic screw.

6. The scan gauge of claim 1, wherein the one or more sloped side walls surround all or a substantial portion of the peripheral edge of the upper surface, and wherein all of the one or more sloped side walls are observable in an intraoral scan when the scan gauge is scanned from substantially above and perpendicular to the upper surface of the elongate body.

7. The scan gauge of claim 1, wherein the sloped side walls are inclined from a direction perpendicular to the upper surface by an angle between about 15° and about 40°.

8. The scan gauge of claim 1, wherein each of the one or more sloped side walls is substantially planar.

9. The scan gauge of claim 1, wherein the one or more sloped side walls define a plurality of interconnected facets, wherein each facet is observable by the intraoral scanner when scanning in a direction substantially perpendicular to the upper surface of the elongate body.

10. The scan gauge of claim 9, wherein the elongate body includes a first end and a second end, and wherein each of the first end and the second end comprises a pointed end, wherein each pointed end is defined by two meeting facets.

11. The scan gauge of claim 1, wherein the one or more identifier markings comprise any one or more of a projection, a recess, or a scannable medium, wherein the identifier markings convey information about the scan gauge.

12. The scan gauge of claim 10, wherein the information comprises any one or more of height, length, width, or dimensional tolerance.

13. The scan gauge of claim 1, further comprising a fiducial marker mounted to or integral with the upper surface of the elongate body.

14. The scan gauge of claim 1, wherein the upper surface of the elongate body includes an aperture or recess configured to receive an indicator element that is identifiable during an intraoral scan.

* * * * *